United States Patent [19]
Zimmerman et al.

[11] 4,208,524
[45] Jun. 17, 1980

[54] N-ALKENYL DECAHYDROISOQUINOLINES

[75] Inventors: Dennis M. Zimmerman, Indianapolis; Winston S. Marshall, Bargersville, both of Ind.

[73] Assignee: Eli Lilly and Company, Indianapolis, Ind.

[21] Appl. No.: 467,707

[22] Filed: May 7, 1974

[51] Int. Cl.$^2$ .................... C07D 217/16; A61K 31/47
[52] U.S. Cl. ...................................... 546/144; 424/258
[58] Field of Search .......... 260/289 D, 289 R, 287 D, 260/289 D; 546/144

[56] References Cited

FOREIGN PATENT DOCUMENTS
802557 11/1973 Belgium ................................... 260/289

OTHER PUBLICATIONS
Sugimoto et al., Chem. Abstracts, vol. 50, col. 1814 b-g (1956).

*Primary Examiner*—Glennon H. Hollrah
*Assistant Examiner*—D. B. Springer
*Attorney, Agent, or Firm*—James L. Rowe; Everet F. Smith

[57] ABSTRACT

1-Alkenyl-3a-substituted-phenyl decahydroisoquinolines, useful as analgetic agonists or analgetic antagonists.

7 Claims, No Drawings

N-ALKENYL DECAHYDROISOQUINOLINES

BACKGROUND OF THE INVENTION

It has long been known that slight chemical modifications of the morphine molecule lead to analgesic agonists of widely differing potency and addictive properties. For example, codeine, the methyl ether of morphine, is a relatively mild analgesic agonist having slight dependance (addiction) liability. On the other hand, heroin, the diacetyl derivative of morphine, is a powerful agonist with extremely high addiction potential. In addition, as long ago as 1915, Pohl found that when the N-methyl group of codeine was replaced with an allyl group, the resulting compound, N-allylnorcodeine, was an opiate antagonist. In 1940, N-allylnormorphine or nalorphine was synthesized and was shown to have a highly specific ability to reverse the depressant effects of morphine. Other simple chemical modifications of the morphine molecule have yielded many interesting drugs. Thus, one fruitful research area in the search for improved analgesics of high potency and/or lower dependance (addiction) liability has been the chemical modification of the morphine molecule.

In addition to modifying the morphine ring structure by chemical means, chemists have developed a second related field of research—the preparation of certain morphine part-structures—with the same end in mind as above; i.e., the synthesis of improved analgesic agonists and/or analgesic antagonists of improved properties. For example, meperidine, a widely used analgesic, can be written as a morphine part-structure. Many other morphine part-structures have been prepared, some of which have improved analgesic agonist properties and others, particularly those with an allyl group attached to a ring nitrogen, have opiate antagonist properties. It had been hoped that morphine part-structure research would produce a compound having both opiate agonist and antagonist properties since the opiate antagonist property would assure a user that the compound would have a greatly reduced dependance liability. Two recently marketed analgesics, pentazocine and phenazocine, have been found to be both antagonists and agonists although they still retain a certain degree of opiate dependance liability.

One potential morphine part-structure can be written as a decahydroisoquinoline with an hydroxyphenyl group substituted on a ring junction carbon atom para to the isoquinoline nitrogen. An attempt to prepare such a compound was described by Boekelheide in a paper appearing in *J. Am. Chem. Soc.*, 69, 790 (1947). This paper set forth the preparation of what, according to the numbering system then in vogue, were 10-phenyldecahydroisoquinolines. It was the author's conclusion, however, that the compound (IX) had a cis configuration and (footnote 5) showed low analgesic activity. The synthesis itself is cumbersome and not free from ambiguity. Sugimoto et. al., *J. Pharm. Soc. Japan*, 75 177 (1955), C.A. 1956 1814b described the synthesis of 8 or 10-alkylated decahydroquinolines. The reference also shows the morphine part-structure, 10-(m-hydroxyphenyl)-3-methylisoquinoline [presently named as 1-methyl-3a-(m-hydroxyphenyl)-1,2,3,3a,4,5,6,7,7a,8-decahydroisoquinoline] but without furnishing a synthesis for it. These authors do not, in fact, describe the preparation of any decahydroisoquinoline, but describe only the preparation of the decahydroquinoline analogs.

Belgian Pat. No. 802,557 issued Jan. 19, 1974, discloses a general method of preparing N-substituted 3a-phenyldecahydroisoquinolines and specifically discloses 3a-phenyl,3a-(m-methoxy phenyl) and 3a-(m-hydroxyphenyl)-1-methyldecahydroisoquinolines, 3a-(m-methoxyphenyl) and 3a-(m-hydroxyphenyl)-1-phenethyldecahydroisoquinolines, and 1-cyclohexylmethyl-3a-phenyldecahydroisoquinoline.

SUMMARY OF THE INVENTION

This invention provides decahydroisoquinolines of Structure I below:

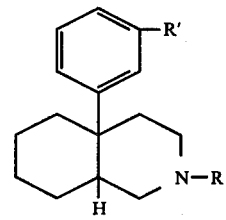

wherein
R is

R' is O-alk, OH or

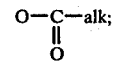

R" and R'" are, separately, H, methyl or ethyl;
alk is ($C_1$–$C_3$) alkyl; and
alken is ($C_2$–$C_5$) alkenyl, the total number of carbon atoms in R being less than 7.

A preferred group of compounds of this invention are those in which R' is O-alk or OH and a particularly preferred group are those in which R' is OH only.

Also included within the scope of this invention are pharmaceutically-acceptable acid addition salts of the above bases formed with non-toxic acids.

In the above formula, the term ($C_2$–$C_5$) alkenyl includes the following groups: vinyl, isobutenyl, 3-methylbut-2-enyl, allyl (prop-2-enyl), methallyl, crotyl, pent-2-enyl, pent-3-enyl, pent-4-enyl, 2-pent-3-enyl, 3-methylbut-2-enyl, 2-methylbut-2-enyl, and the like. Groups illustrative of the scope of R in Formula I, therefore, include the following: isobutenyl, 3-methylbut-2-enyl, allyl, methallyl, crotyl, pent-2-enyl, pent-3-enyl, pent-4-enyl, pent-3-enyl, 3-methylbut-2-enyl, 3-methylpent-2-enyl, 2-methylbut-2-enyl, 4-methylpent-3-enyl, and the like. The term ($C_1$–$C_3$) alk, for which alk is the symbol, includes methyl, ethyl, isopropyl and n-propyl; thus, the term O-alk includes methoxy, ethoxy and the like. Similarly,

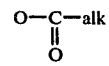

includes acetoxy, propionoxy and butyroxy.

Compounds illustrative of those coming with the scope of Structure I above include the following 1,2,3,3a,4,5,6,7,7a,8-decahydroisoquinolines:

The 1-methylallyl-3a-(m-hydroxyphenyl) compound,
The 1-methallyl-3a-(m-acetoxyphenyl) compound,
The 2-allyl-3a-(m-methoxyphenyl) compound,
The 3a-(m-methoxyphenyl) compound,
The 1-(3-methylpent-2-enyl)-3a-[m-(n-propoxy)phenyl] compound,
The 1-crotyl-3a-(m-ethoxyphenyl) compound,
The 1-(2-pent-3-enyl)-3a-(m-acetoxyphenyl) compound,
The 1-isobutenyl-3a-(m-isobutyroxyphenyl) compound and the like.

Also included within the scope of this invention are the pharmaceutically acceptable salts of the amine bases represented by the above formula formed with nontoxic acids, as for example, salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monhydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The bridgehead substituents, the meta-substituted phenyl at 3a and the hydrogen at 7a, can have either a cis or trans relationship to one another; i.e., the two substituents can be on the same "side" of the decahydroisoquinoline ring system (cis) or on the opposite "side" (trans). In addition, both the 3a and 7a carbon atoms are asymmetric, thus giving rise in each compound to 4 optical isomers, occurring as two racemates designated as the cis-dl and the trans-dl-pair. Additionally, there is a possibility for asymmetry in the sidechain on the ring nitrogen for example, the 1-ethyl-2-but-3-enyl side chain has an asymmetric carbon. The total number of asymmetric centers are increased thereby. There is a further possiblity of geometrical (cis-trans) isomerism (as opposed to optical isomerism) in the ethylenic groups attached to the nitrogen of the decahydroisoquinoline ring. For example, the 3-methylpent-2-enyl group exists in two different geometric forms around the ethylenic bond. Structure I and the compounds listed above exemplifying the scope of Structure I are thus intended to comprehend both the optical isomers, the cis-dl and trans-dl racemates, and their individual enantiomorphs and the structural isomers since, as far as is known, all of the individual isomers and isomer mixtures are useful as analgesic agonists or as analgesic antagonists; albeit large quantitative differences in analgesic agonist or antagonistic potency may exist between related isomers. We prefer, however, those compounds according to structure I above which are in the trans configuration; i.e., the trans-dl racemic pair and the individual trans isomers such as the trans-l compounds.

The compounds of this invention are prepared according to the following procedure using the synthesis of compounds in which R' is methoxyl for purely exemplary purposes:

2-(2-Cyanoethyl)-2-(m-methoxyphenyl) cyclohexanone, prepared by the method of Boekelheide, *J. Am. Chem. Soc.*, 69, 790 (1947), is hydrolysed to 2-(2-carboxyethyl)-2-(m-methoxyphenyl) cyclohexanone. The free acid thus formed is reacted with ethyl chloroformate in the presence of triethylamine which product is in turn reacted with sodium azide. The product of this reaction, an acyl azide, is decomposed under conditions which promote the Curtius rearrangement to yield an isocyanate which, upon refluxing with aqueous acid, yields an imine of Structure III. This reaction sequence is illustrated below:

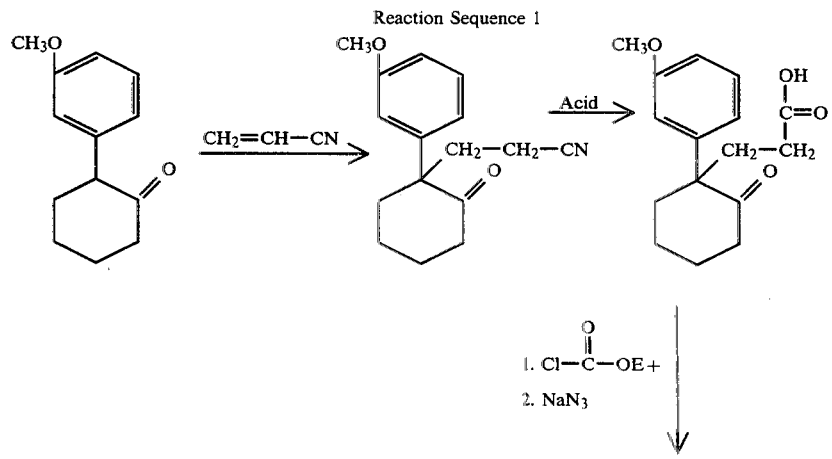

Reaction Sequence 1

Reaction Sequence 1

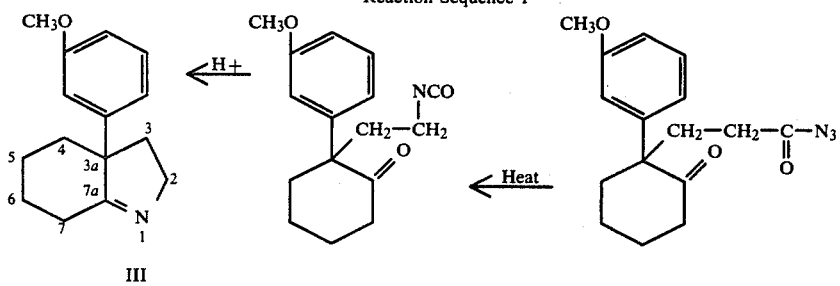

In carrying out the chemical transformations delineated in Reaction Sequence 1, we prefer to hydrolyze the nitrile function of 2-(β-cyanoethyl)-2-(m-methoxyphenyl)-cyclohexanone using a mineral acid in a strongly acidic medium; for example, 12 N aqueous hydrochloric acid in 60–70 percent aqueous acetic acid. Other mineral acids such as sulfuric and phosphoric may also be used, as can a purely aqueous reaction medium, without affecting the yield or purity of the product in any way. Alkaline hydrolysis may also be used, but it is necessary to use somewhat more stringent reaction conditions in order to carry the hydrolysis past the intermediate amide stage to the salt of the free acid. Higher boiling inert solvents such as diethyleneglycol can be used. The second step of the reaction sequence, the formation of an acid chloride from the carboxylic acid of the previous step, can be accomplished by use of any of the milder chlorinating agents, for example, oxalyl chloride, thionyl chloride and the like. We prefer to use ethyl chloroformate. An acid acceptor such as triethylamine can also be used to advantage in forming the desired acid chloride, using an inert solvent. The reaction of the thus formed acid chloride with sodium azide to form the acid azide is carried out under standard conditions. It should be recognized, however, that an alternate procedure for preparing the azide exists; i.e., the formation of the hydrazide by reaction of anhydrous hydrazine with the acid chloride followed by azide formation with nitrous acid. Rearrangement of the azide under Curtius rearrangement conditions, consisting simply in heating the azide, however synthesized, at the reflux temperature of benzene or toluene for from 1 to about 24 hours, yields the expected isocyanate. Acidification of the isocyanate product yields directly a 3H-indole (III). The acidification is carried out by heating the isocyanate with a concentrated mineral acid as for example hydrochloric or sulfuric acid for from 12–24 hours. The product, as the free base, is isolated by basifying the acid reaction medium with, for example, sodium hydroxide, sodium carbonate or the like.

Structure III above is named 3a-(m-methoxyphenyl)-3H-indole or 3a-(m-methoxyphenyl)-3H-benzo[b]pyrrole and was prepared by Langlois et al. Tetrahedron, 27, 6451 (1971) using a different method of synthesis.

Reaction Sequence 2 below outlines the production of the compounds of this invention represented by Structure I, from the intermediates of Reaction Sequence 1. The 3H-indole (III) end product of Reaction Sequence 1 is methylated quantitatively to yield an iminium salt (IIIa) which compound is next reacted, also quantitatively, with diazomethane to yield an aziridinium salt (IV). The aziridinium salt rearranges to produce a mixture of double-bond isomers (Va and Vb). Reduction of the enamine isomer (Va) with sodium borohydride in acetic acid yields a decahydroisoquinoline-VI or VIa-(I above in which R' is methoxy).

The trans-dl-racemate, (VI), is the predominant racemate isolated from this reaction with only minor quantities of the cis-dl-racemate [cis-dl-1-methyl-3a-(m-methoxyphenyl)-1,2,3,3a,4,5,6,7,7a,8-decahydroisoquinoline] (VIa) being found. Platinum hydrogenation also yields predominantly the trans-dl-racemate. On the other hand, hydrogenation of the enamine (Va) with 5 percent palladium-on-carbon yields a mixture of the cis-dl- and trans-dl racemates (40–60), which racemates are readily separated from each other by precipitating the trans-dl racemate as a picrate salt. The cis-dl racemate does not form an insoluble picrate. The above series of reactions is illustrated below in Reaction Sequence 2:

Reaction Sequence 2

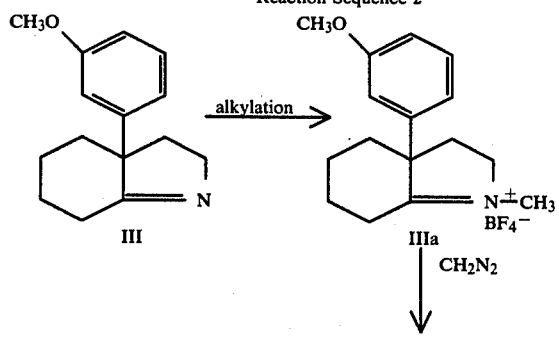

-continued

Reaction Sequence 2

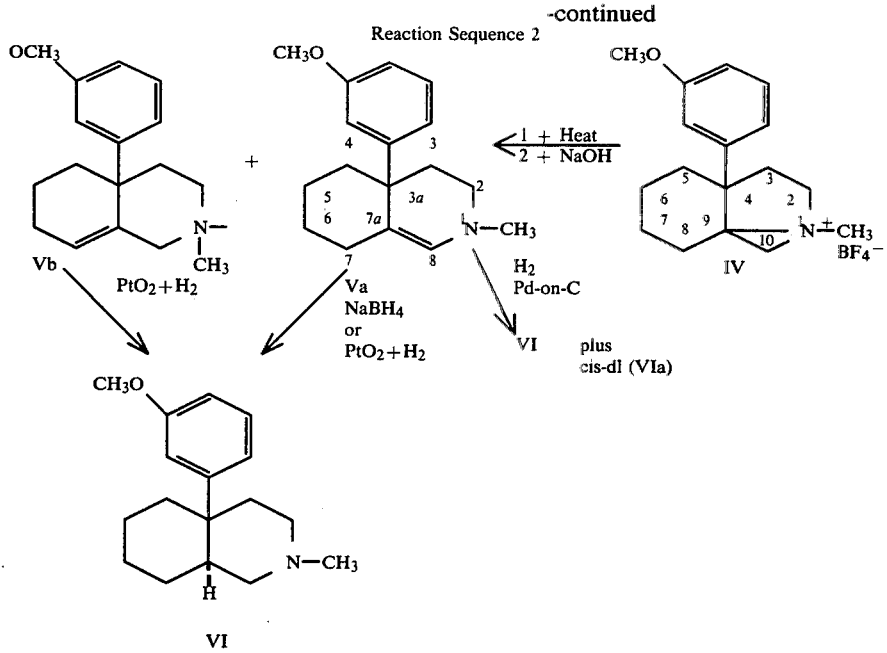

In carrying out the procedures outlined in Reaction Sequence 2, above, alkylation of the 3H-indole (III) to yield the quaternary methyl derivative (IIIa) is carried out preferably by treating the indole with trimethyloxonium tetrafluororate. Other alkylating agents can, however, be used as for example dimethyl sulfate, methyl iodide and the like. The product of this methylation reaction, an iodide or sulfate salt, is then metathesized to the fluoroborate salt by reaction with fluoroboric acid. Transformation of this quaternary salt to an aziridinium salt (IV) named systematically as a salt of 1-azonia-1-methyl-4-phenyl (or meta-substituted phenyl)tricyclo [4,2,1,0$^{1-9}$] decane), is accomplished by reacting the iminium salt with diazomethane. The diazomethane can be generated in situ or added as a solution in accordance with procedures long established in the art. The aziridinium salt is rearranged to yield a mixture of double-bond isomers (Va and Vb) (85-15) by heating, preferably for about 1 hour at about 200° C. although longer reaction times at somewhat lower temperatures will give essentially the same yields. The direct product of the rearrangement is an amine salt which must be treated with a base such as sodium hydroxide or sodium carbonate in order to provide the thus produced N-methyl octahydroisoquinolines (Va and Vb) as free bases. The reduction of the (Va and Vb) to the corresponding decahydroisoquinolines (VI and VIa) has been discussed above.

Compounds according to structure VI or VIa containing a meta-hydroxyphenyl substituent at C-3a are prepared from the corresponding methoxy compound by dealkylation using, for example, hydrobromic acid in acetic acid.

The preparation of compounds according to Formula I can be accomplished by several procedures. As a starting point, the N-methyl derivative (VI above) can be reacted with phenylchloroformate to yield a carbamate. Hydrolysis of this carbamate provides the secondary amine (I wherein R is H). Alkenylation of the secondary amine by standard procedures using a suitable alkenyl halide readily yields the compounds of this invention according to I above wherein R is an alkenyl group as defined. p Alternatively, an amide can be formed with the secondary amine function (I where R is H) with an acylating agent

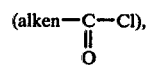

and the resulting amide reduced to a tertiary amine function with LiAlH$_4$ or other similar reducing agent, to yield compounds according to I in which both R" and R'" are hydrogen.

Compounds according to I above in which R' is O-alk, alk being other then methyl, can be prepared either by employing as a starting material a 2-(2-cyanoethyl)-2-(m-alkoxyphenyl) cyclohexanone in which the alkoxy group is ethoxy or propoxy, or can be derived from the m-hydroxyphenyl derivative by any standard phenolic ether synthesis.

Compounds according to I above in which R' is

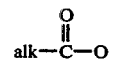

are prepared by standard acylation procedures from the corresponding compound in which R' is OH, such acylation procedures involving, for example, the reaction of an anhydride

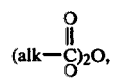

a mixed anhydride,

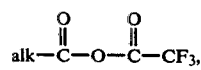

or an acid chloride alk-C-Cl, with the phenol or preferably, an alkali metal salt thereof.

This invention is further illustrated by the following specific examples.

EXAMPLE 1

A mixture was prepared containing 368 g. of 2-(β-cyanoethyl)-2-(m-methoxyphenyl)cyclohexanone, 2000 ml. of glacial acetic acid, 850 ml. of 12 N aqueous hydrochloric acid and 850 ml. of water. The mixture was refluxed for about 19 hours and then cooled to room temperature. Sufficient ice and water were added to make a volume of about 11 liters. The resulting mixture was stirred for about 30 minutes at which point a precipitate comprising 2-(β-carboxyethyl)-2-(m-methoxyphenyl)cyclohexanone formed. The supernate was removed by centrifugation, and the precipitate collected. The precipitate was thoroughly washed with water and then dried to yield about 280 g. of 2-(β-carboxyethyl)-2-(m-methoxyphenyl)cyclohexanone melting at about 143°–4° C. after recrystallization from water.

About 225 g. of 2-(β-carboxyethyl)-2-(m-methoxyphenyl)-cyclohexanone were mixed with 125 g. of triethylamine and about 20 g. of sodium sulfate. A solution of 99 g. of ethyl chloroformate in 3250 ml. of anhydrous ether was added in dropwise fashion. The reaction mixture was stirred for about 1 hour at about 0° C. at which point 89 g. of sodium azide in 350 ml. of water were added in dropwise fashion. After the addition had been completed, the reaction mixture was stirred for an additional two hours at 0° C. The organic layer was separated. 2-(β-Azidoformylethyl)-2-(m-methoxyphenyl)-cyclohexanone formed in the above reaction was isolated as an oil by evaporation of the ether in vacuo. The residual oil was dissolved in 3.5 l. of benzene, and the solution heated at refluxing temperature for about 1.5 hours. The benzene was removed by evaporation in vacuo. By this procedure the azidoformyl group was rearranged under Curtius conditions to yield the corresponding isocyanate. The benzene was removed by evaporation in vacuo. The residual isocyanate was next hydrolyzed to the cyclic imine by heating overnight in a mixture containing 1200 ml. of water, 1200 ml. of glacial acetic acid and 1200 ml. of 12 N aqueous hydrochloric acid. The hydrolysis mixture was cooled and then made strongly basic with 50 percent aqueous sodium hydroxide. 3a-(m-methoxyphenyl)-2,3,3a,4,5,6,7-heptahydroindole thus procuced was extracted into ether, and the ether layer separated, washed with water and dried. Evaporation of the ether layer to dryness yielded 153.2 g. of 3a-(-m-methoxyphenyl)-2,3,3a,4,5,6,7-heptahydroindole, distilling at about 140° C. at 0.07 mm/Hg. (For comparison, see Langlois et al., *Tetrahedron*, 27, 5641 (1971) compound 10 and page 5647, table 4, compound 42).

About 341 g. of 3a-(m-methoxyphenyl)-2,3,3a,4,5,6,7-heptahydroindole were dissolved in 600 ml. of methyl ethyl ketone. 184 g. of dimethyl sulfate were added to this solution in dropwise fashion. The reaction mixture was heated at refluxing temperature for one hour. 1100 ml. of water were then added over a one-half hour period and the reaction mixture refluxed for another three hours. The reaction mixture was made strongly basic with 50 percent aqueous sodium hydroxide with external cooling provided. 1-Methyl-3a-(m-methoxyphenyl)-1,2,3,3a,4,5,6-heptahydroindole formed in the above reaction, being insoluble in the alkaline layer, separated and was extracted into ether. The ether extract was separated, washed with water and dried. Evaporation of the ether in vacuo left a residual oil comprising 1-methyl-3a-(m-methoxyphenyl)-1,2,3,3a,4,5,6-heptahydroindole at about 144° C. at 0.4 mm/Hg; yield=325.4 g.

325.4 g. of 1-methyl-3a-(m-methoxyphenyl)-1,2,3,3a,4,5,6-heptahydroindole were dissolved in 2500 ml. of ether. A 50 percent mixture of 50 percent fluoroboric acid and anhydrous ethanol was added in dropwise fashion with stirring until the solution was acid to congo red. The ether layer was separated by syphoning. The aqueous layer which contained 1-methyl-3a-(m-methoxyphenyl)-2,3,3a,4,5,6,7-heptahydroindolinium fluoborate formed in the above reaction was allowed to stand while the fluoborate salt slowly crystallized. The salt was collected by filtration, and the filter cake washed with ether. The filter cake was then triturated with an anhydrous ethanol-ether solvent mixture. The solvent was separated by filtration, and the filter cake was dried. Yield of the fluoroborate salt was about 392 g.

A solution of 55 g. of 1-methyl-3a-(m-methoxyphenyl)-2,3,3a,4,5,6,7-heptahydroindolinium fluoborate in 500 ml. of methylene chloride was cooled to about 0° C. A solution of diazomethane prepared from 103 g. of N-methyl-N-nitroso-p-toluenesulfonamide in ether was added over a five-hour period. The reaction mixture was allowed to warm to room temperature and was stirred overnight. The supernate was separated from the precipitated oil comprising the fluoborate salt of the corresponding aziridinium compound, 1-azonia-1-methyl-4-(m-methoxyphenyl)tricyclo[4,2,1,0$^{2-8a}$] decane. The oil residue was triturated with three 1000 ml. portions of ether, and the ether washes were discarded. The residual oil was transferred to a 500 ml. round-bottom flask and heated at atmospheric pressure for about one hour at 200° C., thus forming 1-methyl-3a-(m-methoxyphenyl)-1,2,3,3a,4,5,6,7-octahydroisoquinoline, which compound was dissolved in anhydrous ethanol, and the ethanol solution treated with an excess of 50 percent aqueous sodium hydroxide and water. The octahydroisoquinoline, being insoluble in the alkaline solution, separated and was extracted into ether. The ether extract was separated and dried, and the ether removed therefrom by evaporation in vacuo. 1-methyl-3a-(m-methoxyphenyl)-1,2,3,3a,4,5,6,7-octahydroisoquinoline thus prepared distilled at about 168° C. at 0.5 mm/hg.

A mixture was prepared containing about 163 g. of 1-methyl-3a-(m-methoxyphenyl)-1,2,3,3a,4,5,6,7-octahydroisoquinoline, 90 g. of sodium borohydride and 4500 ml. of tetrahydrofuran was cooled to about 5° C. 1630 ml. of acetic acid were added in dropwise fashion while maintaining the temperature below about 10° C. The mixture was stirred for one-half hour at about 5° C. and then gradually warmed to refluxing temperature with mild heating. The mixture was refluxed for one hour, and was then made strongly basic with about 3 liters of 25 percent aqueous sodium hydroxide. The tetrahydrofuran layer was decanted, and the aqueous layer washed with three two-liter portions of ether. The ether and tetrahydrofuran layers were combined and evaporated to dryness in vacuo. The resulting residue, comprising 1-methyl-3a-(m-methoxyphenyl)-1,2,3,3a,4,5,6,7,7a,8-decahydroisoquinoline formed in the above reaction was dissolved in about 3.5 l of ether, and the ethereal layer washed with three 2 l. portions of water. The ether layer was dried, and the ether removed therefrom by evaporation to dryness in vacuo. The yield of the decahydroisoquinoline was 162.3 g.

The compound was purified via the picrate salt which was converted back to the free base by refluxing the salt with saturated lithium hydroxide at the ratio 30 g. of picrate to 1000 ml. of saturated aqueous lithium hydroxide solution. Extraction of the free base into benzene followed by distillation of the base yielded 1-methyl-3a-(m-methoxyphenyl)-1,2,3,3a,4,5,6,7,7a,8-decahydroisoquinoline boiling in the range 145°–79° C. at 0.1 mm/Hg. The corresponding picrate salt melted at about 161°–2° C. after recrystallization from aqueous ethanol. Overall yield through the sodium borohydride reduction procedure was about 90 percent.

Alternatively, 1-methyl-3a-(m-methoxyphenyl)-1,2,3,3a,4,5,6,7-octahydroisoquinoline was reduced over platinum oxide with hydrogen to yield the corresponding decahydroisoquinoline. 66.7 g. of the octahydro compound were dissolved in 650 ml. of absolute ethanol. 5 g. of platinum oxide catalyst were added, and the hydrogenation mixture subjected to 60 psi of hydrogen. The yield of 1-methyl-3a-(m-methoxyphenyl)-1,2,3,3a,4,5,6,7,7a,8-decahydroisoquinoline synthesized by this procedure was about 96 percent. The compound was again isolated as the picrate salt.

The 1-methyl group was cleaved from the above decahydroisoquinoline by dissolving 8 g. of 1-methyl-3a-(m-methoxyphenyl)-1,2,3,3a,4,5,6,7,7a,8-decahydroisoquinoline in 64 ml. of methylene chloride and adding thereto a solution of 5.6 g. of phenyl chloroformate in 16 ml. of methylenechloride. The resulting mixture was refluxed for about two hours, and allowed to stand overnight. The solvents were then evaporated in vacuo. 100 ml. of 5 percent aqueous sodium hydroxide were added, and the resulting mixture stirred with warming for about 15 minutes. 1-Phenylcarboxy-3a-(m-methoxyphenyl)-1,2,3,3a,4,5,6,7,7a,8-decahydroisoquinoline formed in the above reaction, being insoluble in the basic layer, separated and was extracted into ether. The ether extract was separated and washed with water. The ether extract was in turn extracted with 250 ml. of 10 percent aqueous hydrochloric acid followed by 250 ml. of water to remove any unreacted N-methyldecahydroisoquinoline. The ether layer was separated, dried, and the ether removed by evaporation. The residue was refluxed for 66 hours in 240 ml. of anhydrous ethanol and 50 ml. of 50 percent aqueous potassium hydroxide. The volatile constituents were removed in vacuo and the resulting concentrate extracted with ether. The ether extract was separated and dried. Evaporation of the ether left a residue comprising 1-phenylcarboxy-3a-(m-methoxyphenyl)-1,2,3,3a,4,5,6,7,7a,8-decahydroisoquinoline which was dissolved in 250 ml. of 10 percent aqueous hydrochloric acid. The acid layer was washed with ether, and the ether wash was discarded. The aqueous layer was made strongly basic with 50 percent sodium hydroxide, and 3a-(m-methoxyphenyl)-1,2,3,3a,4,5,6,7,7a,8-decahydroisoquinoline thus formed was extracted into ether. The ether layer was separated, dried and the ether removed therefrom by evaporation. Distillation of the resulting residue yielded 5.5 g. of 3a-(m-methoxyphenyl)-1,2,3,3a,4,5,6,7,7a,8-decahydroisoquinoline boiling at about 148° C. at 0.2 mm/Hg.

3a-(m-methoxyphenyl)-1,2,3,3a,4,5,6,7,7a,8-decahydroisoquinoline was converted to the corresponding 3a-(m-hydroxyphenyl) derivative by treatment with 50 percent HBr in 50 percent aqueous acetic acid. In this procedure, 5.2 g. of freshly distilled 3a-(m-methoxyphenyl)-1,2,3,4,5,6,7,7a,8-decahydroisoquinoline were dissolved in 40 ml. of 50 percent aqueous hydrobromic acid and 40 ml. of 50 percent aqueous acetic acid. The resulting mixture was refluxed for 18 hours. The reaction mixture was cooled, diluted with about 250 ml. of water and the pH thereof adjusted to about 10.4 with 50 percent aqueous sodium hydroxide. The reaction mixture was treated with a 3:1 n-butanol-benzene solvent system. 3a-(m-Hydroxyphenyl)-1,2,3,3a,4,5,6,7,7a,8-decahydroisoquinoline being insoluble in the alkaline layer passed into the organic layer. The organic layer was separated and dried, and the solvents removed therefrom by evaporation in vacuo. 5 g. of 3a-(m-Hydroxyphenyl)-1,2,3,3a,4,5,6,7,7a,8-decahydroisoquinoline were obtained which melted at about 212°–214° C. with decomposition after recrystallization from dimethylformamide.

Analysis Calc.: C, 76.67; H, 9.65; N, 6.39. Found: C, 76.88; H, 9.35; N, 6.24.

EXAMPLE 2

Following the procedure of the above example, 1-methyl-3a-(m-methoxyphenyl)-1,2,3,3a,4,5,6,7,7a,8-decahydroisoquinoline was demethylated with a mixture of 50 percent aqueous hydrobromic acid and 50 percent aqueous acetic acid to yield 1-methyl-3a-(m-hydroxyphenyl)-1,2,3,3a,4,5,6,7,7a,8-decahydroisoquinoline melting at about 202°–4° C. after recrystallization from acetonitrile.

Analysis Calc.: C, 78.32; H, 9.45; N, 5.71. Found: C, 78.37; H, 9.17; N, 6.00.

The compound can be N-demethylated by the procedure of Example 1 to yield 3a-(m-hydroxyphenyl)-1,2,3,3a,4,5,6,7,7a,8-decahydroisoquinoline.

EXAMPLE 3

A mixture was prepared from 2.31 g. of 3a-(m-hydroxyphenyl)-1,2,3,3a,4,5,6,7,7a,8-decahydroisoquinoline, 1.22 g. of allyl bromide, 1.20 g. of sodium bicarbonate and 30 ml. of dimethylformamide. The reaction mixture was heated to refluxing temperature for about one hour. After the reaction mixture had cooled, it was diluted with ice water. 1-Allyl-3a-(m-hydroxyphenyl)-1,2,3,4a,4,5,6,7,7a,8-decahydroisoquinoline formed in the above reaction, being insoluble in water, was extracted into ether. The ether extract was separated, dried, and the ether removed by evaporation to dryness in vacuo. 1-Allyl-3a-(m-hydroxyphenyl)-1,2,3,3a,4,5,6,7,7a,8-decahydroisoquinoline thus prepared melted at about 146°–8° C. after recrystallization from ethyl acetate. For $C_{18}H_{25}NO$ Analysis Calc.: C, 79.66; H, 9.29; N, 5.16. Found: C, 79.55; H, 9.11; N, 4.88.

Following the above procedure, 1-(3-methyl-but-2-enyl)-3a-(m-hydroxyphenyl)-1,2,3,3a,4,5,6,7,7a,8-decahydroisoquinoline. M.P. 113°–5° C. (free base) was also prepared.

Analysis: Calc. for $C_{20}H_{29}NO$; C, 80.22; H, 9.76; N, 4.68. Found: C, 79.95; H, 10.02; N, 4.42.

Other compounds of this invention can be prepared according to the above procedure by substituting the 3a-(m-methoxyphenyl) derivative for 3a-(m-hydroxyphenyl)-1,2,3,3a,4,5,6,7,7a,8-decahydroisoquinoline in the above example or by substituting methallyl bromide, crotyl bromide, hex-2-enyl bromide, pent-2-enyl bromide or the like alkenyl halide for allyl bromide.

As previously stated, the compounds of this invention represented by Formula I above when R is free from asymmetric carbon atoms contain two asymmetric centers, at 3a and 7a. Thus the compounds can exist as four diastereoisomers occurring as two racemic pairs, commonly designated as the cis-dl and the trans-dl racemates. Any given racemic pair can be resolved into its optical antipodes by treatment of the racemate with an optically active acid as for example L(+)-mandelic acid or D(−)-mandelic acid.

In carrying out such a procedure, one-half mole of an optically-active mandelic acid in solution is added to a solution of a mole of, for example, trans-dl-1-(3-methylbut-2-enyl)-3a-(m-hydroxyphenyl)-1,2,3,3a,4,5,6,7,7a,8-decahydroisoquinoline. The salt of L(+)-mandelic acid and the trans-1(−)-decahydroisoquinoline isomer precipitates and is isolated. The free base is readily obtained from the salt by standard procedures.

EXAMPLE 4

Preparation of Salts

Salts of the free bases of this invention, other than the mandelate salts whose preparation is illustrated above, are prepared by dissolving the free base in ether and adding an equivalent of a suitable non-toxic acid, also in ether. The salts thus formed, as for example the sulfate and phosphate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include the hydrochloride, sulfate, hydrobromide, phosphate, hydrogen phosphate, dihydrogen phosphate, acetate, maleate, succinate, tartrate, citrate, benzoate, and p-toluene sulfonate salts of the N-alkenyl 3a-(m-hydroxyphenyl)-1,2,3,3a,4,5,6,7,7a,8-decahydroisoquinolines of this invention and the corresponding m-alkoxy and m-acyloxy derivatives.

As previously stated, the compounds of this invention have both analgesic agonist and analgesic antagonist properties. While the compounds are capable of producing analgesia in mammals, the added characteristic of being simultaneously analgesic-antagonistic greatly decreases the addition liability of the particular drug. It might be said that the analgesic-antagonist activity of the compounds of this invention acts as a built-in safety device tending to mitigate any addictive properties of the drug caused by its opiate-like analgesic action. Thus, the compounds can be used to produce analgesia with minimal physical dependance liability.

The compounds of this invention demonstrate their analgesic activity in the mouse-writhing test and in the rat tail jerk assay, both standard assays for analgesic action. For example, 1-allyl-3a-(m-hydroxyphenyl)-1,2,3,3a,4,5,6,7,7a,8-decahydroisoquinoline inhibits writhing induced in mice by the intraperitoneal injection of acetic acid. With the compound injected by the subcutaneous route, the following results were obtained: 100 mg./kg., 87 percent inhibition; 20 mg./kg., 70 percent inhibition; 5 mg./kg., 57 percent inhibition; 2 mg./kg., 67 percent inhibition (all readings made at one-half hour). By the oral route, the compound showed the following activity: 81 percent inhibition at 100 mg./kg. dose; 45 percent inhibition at a 20 mg./kg. dose (all readings made at one-half hour). Naloxone was found to totally prevent the inhibitory action of the compound at the 20 mg./kg. level, thus demonstrating that the compound is an opiate-type analgesic. In the above tests, the compound was administered as a suspension. When the compound was solubilized as the hydrochloride salt, it was somewhat more active in the mouse writhing assay showing an $ID_{50}$ (dose which gives 50 percent inhibition of writhing) of less than 0.5 mg./kg. by the subcutaneous route. When a solution of the compound was injected, there was an early peaking of the analgesic activity with a maximum activity being found at from 10 to 15 minutes after injection. The oral $ID_{50}$ was about 20 mg./kg. when using a solution of the compound as the hydrochloride salt.

In the rat tail jerk assay, 1-allyl-3a-(m-hydroxyphenyl)-1,2,3,3a,4,5,6,7,7a,8-decahydroisoquinoline gave a significant increase in reaction time at dose levels of 80 mg./kg. both subcutaneously and orally. Analgesic-antagonist studies carried out with the same compound demonstrated that the compound when given to rats orally at a dose level of 50 mg./kg. 30 minutes before testing was able to decrease the increased reaction time produced by morphine given at a dose level of 5 mg./kg. subcutaneously 10 minutes prior to test. Actually, the reaction time was less than the reaction time for morphine alone and considerably less than the postulated reaction time produced by the additive effects of administering the two analgesics. The compound by itself produced significant increases in reaction times at dosages of 25 and 50 mg./kg. subcutaneously although some side effects were present. When the compound was administered at a 50 mg./kg. level subcutaneously 120 minutes prior to testing and the morphine administered at the rate of 5 mg./kg. subcutaneously 10 minutes prior to testing, there was a significant decrease in the reaction time over that produced by morphine alone when administered by the same route and without any evidence of side effects, clear cut evidence of analgesic antagonism.

Similarly, 1-(3-methylbut-2-enyl)-3a-(m-hydroxyphenyl)-1,2,3,3a,4,5,6,7,7a,8-decahydroisquinoline was shown to inhibit acetic acid-induced writhing in mice at oral dosages of 100 mg./kg. (80 percent inhibition); and 50 mg./kg. (42 percent inhibition), and subcutaneously at 20 mg./kg. (85 percent inhibition), 10 mg./kg. (79 percent inhibition), and 5 mg./kg. (71 percent inhibition). (All measurements taken at one-half hour.) This compound is apparently rather short-acting because of the fact that when the assay was carried out at one and a half or three hours after drug injection, no statistically significant inhibition of writhing was found. Using a water solution of the hydrochloride salt of the compound, an $ID_{50}$ of less than 5 mg./kg. was found for administration by the subcutaneous route with a 15 minute peak. The $ID_{50}$ orally was in the range 50–100 mg./kg. In the rat tail jerk assay, a dose of 80 mg./kg. by the subcutaneous route at one-half hour gave a statistically significant increase in reaction time, the increase being maximal at this dose level. Further studies using the rat jerk assay procedure indicated that a dose level of 25 mg./kg orally gave statistically significant increases in reaction time when measured 10 minutes to one hour after injection. The minimum effective dose for the compound administrated as an aqueous solution of the hydrochloride salt measured 30 minutes after injection was found to be 2 mg./kg. by the subcutaneous route. In analgesic-antagonist studies, a dosage of 20 mg./kg. subcutaneously given two hours prior to testing was able to decrease the increase in reaction time attributable to a subcutaneous dose of 5 mg./kg. of morphine given 10 minutes before a test without side effects.

The compounds of this invention can be employed to produce analgesia in mammals by administration via either the parenteral or oral route. For oral dosage, a suitable quantity of a pharmaceutically-acceptable salt of a base according to Formula I, formed with a non-toxic acid, is mixed with starch or other excipient, and the mixture placed in telescoping gelatin capsules each containing an analgesic dose. Similarly, the salt can be mixed with starch, a binder, a lubricant, and the mixture compressed into tablets each containing a standard analgesic dose. The tablets may be scored if lower or divided dosages are to be used. With parenteral administration, the intramuscular or subcutaneous routes are preferred. For this purpose, aqueous solutions or suspensions are employed using a pharmaceutically-acceptable salt of the amine base of formula 1. In general, modes of administration and pharmaceutical forms found useful in the past for morphine, codeine, methadon, meperidine and other opiate-like analgesics can be adopted by those skilled in the art for the compounds of this invention.

We claim:

1. A compound of the formula:

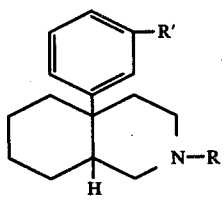

wherein

R is

R' is O-alkyl or OH;
R'' and R''' are, separately, H, methyl or ethyl; alkyl is ($C_1$-$C_3$) alkyl; and
alken is ($C_2$-$C_5$) alkenyl, the total number of carbon atoms in R being less than 7.

2. A pharmaceutically-acceptable salt of an amine base according to claim 1.

3. A compound according to claim 1, said compound being 1-allyl-3a-(m-hydroxyphenyl)-1,2,3,3a,4,5,6,7,7a,8-decahydroisoquinoline.

4. A compound according to claim 1, said compound being 1-(3-methylbut-2-enyl)-3a-(m-hydroxyphenyl)-1,2,3,3a,4,5,6,7,7a,8-decahydroisoquinoline.

5. A tran-dl racemate of a compound according to claim 1.

6. A trans-dl racemate of a compound according to claim 1 in which R' is OH.

7. A compound of the formula

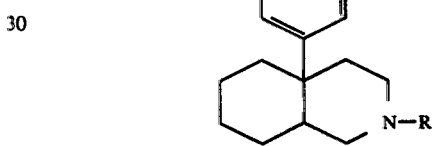

wherein
R' is —OH or —OCH$_3$
R is —CH$_2$—CH=CH$_2$ or —CH$_2$—CH=C(CH$_3$)$_2$

* * * * *